(12) United States Patent
Zunker

(10) Patent No.: US 6,911,001 B2
(45) Date of Patent: Jun. 28, 2005

(54) RECEPTACLE FOR APPLICATOR FOR INCONTINENCE INSERT

(76) Inventor: MaryAnn Zunker, 2686 Yorkton Pl., Oshkosh, WI (US) 54904

( * ) Notice: Subject to any disclaimer, the term of this patent is extended or adjusted under 35 U.S.C. 154(b) by 21 days.

(21) Appl. No.: 10/328,425

(22) Filed: Dec. 23, 2002

(65) Prior Publication Data

US 2004/0122284 A1 Jun. 24, 2004

(51) Int. Cl.[7] .............................. A61F 2/00; B68D 85/00
(52) U.S. Cl. ........................ 600/29; 206/459.5; 206/581
(58) Field of Search ...................... 600/21–31; 206/223, 206/371, 572, 363–365, 312, 438, 443, 459.1, 454.5, 449, 564, 557, 561, 362, 635, 440, 459.5, 494, 578, 577, 581; 220/578, 4.01, 4.21, 4.26, 553

(56) References Cited

U.S. PATENT DOCUMENTS

| | | | | |
|---|---|---|---|---|
| 3,519,123 A | * | 7/1970 | Rich et al. .................. | 206/362 |
| 3,561,596 A | * | 2/1971 | Knox .......................... | 206/229 |
| 4,848,588 A | * | 7/1989 | Rasmussen ................. | 206/581 |
| 4,927,025 A | * | 5/1990 | Thompson et al. ......... | 206/575 |
| 5,289,919 A | * | 3/1994 | Fischer ....................... | 206/571 |
| 5,456,352 A | * | 10/1995 | McQueeny ................ | 206/223 |
| 5,931,304 A | * | 8/1999 | Hammond .................. | 206/570 |
| 5,964,741 A | * | 10/1999 | Moder et al. ............... | 604/358 |
| 6,056,714 A | * | 5/2000 | McNelis et al. ............. | 604/14 |
| 6,454,095 B1 | * | 9/2002 | Brisebois et al. ........... | 206/494 |
| 2002/0063076 A1 | | 5/2002 | Kolterjohn et al. | |

FOREIGN PATENT DOCUMENTS

| | | |
|---|---|---|
| CA | 2 109 782 A | 5/1995 |
| DE | 88 14 059 U | 12/1988 |
| DE | 195 27 393 A | 2/1997 |
| WO | WO 96/20683 A1 | 7/1996 |
| WO | WO 02/17844 A2 | 3/2002 |
| WO | WO 02/26159 A1 | 4/2002 |
| WO | WO 02/30347 | 4/2002 |

* cited by examiner

Primary Examiner—Samuel G. Gilbert
(74) Attorney, Agent, or Firm—Kimberly-Clark Worldwide, Inc.; G. Peter Nichols

(57) ABSTRACT

A receptacle for storing and dispensing applicators for incontinence inserts. The receptacle includes at least one first individual package containing a carriage and including a first reference indicator and at least one second individual package containing a plunger that mates with the carriage to dispense an incontinence insert disposed within the carriage and including a second reference indicator.

18 Claims, 2 Drawing Sheets

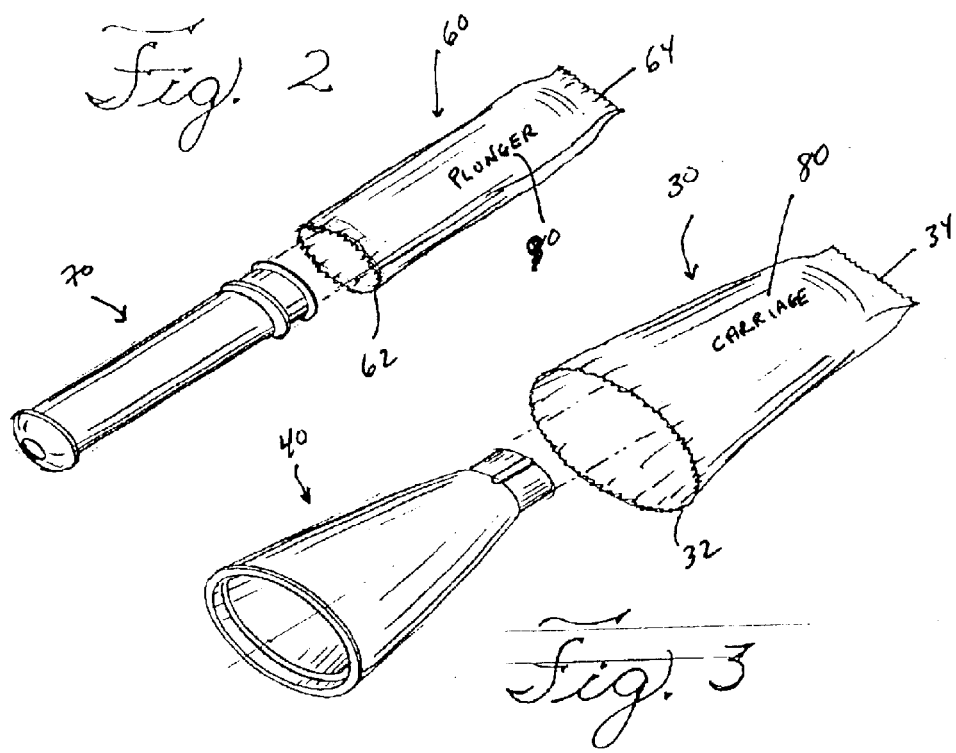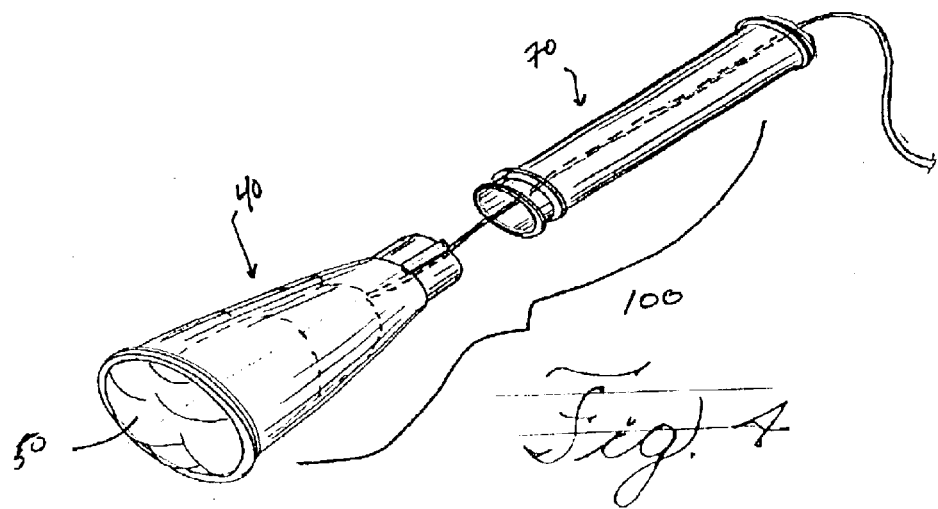

RECEPTACLE FOR APPLICATOR FOR INCONTINENCE INSERT

BACKGROUND OF THE INVENTION

The present invention generally relates to a receptacle for an applicator for an incontinence insert. The components of the applicator, i.e., the carriage and the plunger, are separately packaged and contain a reference indication so that the consumer can easily distinguish the plunger from the carriage and can easily distinguish the components of the applicator from sanitary absorbent articles. Ideally, the receptacle of the present invention contains plungers that may be reused and therefore the receptacle may contain a number of plungers that is less than the number of carriages.

Sanitary absorbent articles are large-scale commercially manufactured articles used to absorb and retain bodily exudates. Such articles are convenient because they are economical yet disposable; they include sanitary napkins, infant diapers, adult incontinence pads, panty liners, tampons and the like.

Sanitary absorbent articles and particularly feminine sanitary napkins are made available to the consumer in receptacles containing a plurality of sanitary napkins. Traditionally, the industry has used receptacles in the form of cardboard boxes. In more recent years the cardboard box has gradually been replaced by a bag of plastic material. The sanitary napkins held in a receptacle, either a cardboard box or a bag of plastic material, are individually packaged. This feature allows the user to transport a sanitary napkin outside the protective environment of the receptacle, such as in a purse or pocket, while keeping the sanitary napkin free from dirt, stains or impurities. The typical packaging is in the form of a pouch of plastic material in which the sanitary napkin is placed. Immediately before use, the wearer removes the sanitary napkin from the pouch and installs it in the crotch portion of the undergarment. The pouch is then discarded.

Although the packaging described above is useful, differentiation and proper selection of sanitary absorbent articles on the store shelves is difficult because of the many choices of products and manufacturers. In addition, many users carry in their purse or pocket one or more of the individually packaged sanitary absorbent articles. As a result, the user must remove the package and visually inspect it to determine whether the package contains the desired absorbent article.

Compounding these present problems, in the near future, it is anticipated that incontinence inserts will be commercially available. Incontinence inserts are being developed to address then need for a non-surgical procedure and/or device to reduce the involuntary urine loss commonly associated with "stress urinary incontinence." One way to alleviate the problem of incontinence is to place an insert within the vagina to allow the urethra to compress and/or provide support for the bladder neck in order to prevent the involuntary loss of urine. Inserts developed for such purposes are disclosed in for example, U.S. Pat. Nos. 6,090,038; 6,090,098; and 6,142,928, the relevant portions of which are incorporated herein by reference. To properly deliver these and other incontinence inserts, applicators have been developed and examples of applicators are disclosed in commonly assigned, co-pending applications, U.S. Ser. No. 09/675,458, and 10/274,855, the relevant portions of which are incorporated herein by reference.

As a result of the anticipated commercial introduction of incontinence inserts, there is a need in the industry to develop a receptacle for applicators for incontinence inserts and for a reference system to allow the user to identify the components of the applicator and to distinguish the applicator or its components from sanitary absorbent articles.

SUMMARY OF THE INVENTION

In response to the above need, the present invention provides a receptacle for storing at least one applicator for an incontinence insert. The receptacle contains a first individual package and a second individual package. The first individual package contains a carriage and includes a first reference indicator. The carriage carries an incontinence insert. The second individual package contains a plunger and includes a second reference indicator. The plunger mates with the carriage so that the incontinence insert can be dispensed. Desirably, the first reference indicator and the second reference indicator differ so that the user can distinguish between the carriage and the plunger and can distinguish each from, for example, sanitary absorbent articles.

Each of the first reference indicator and the second reference indicator is selected from the group consisting of visual indicators, tactile indicators, or a combination of both. Visual indicators include, but are not limited to color, written notice or indicia, pictograph, icon, or a combination of the above. Tactile indicators include texturing (e.g., knurling), the use of differing materials, embossing, or a combination. The first reference indicator may be provided on the first individual package, the carriage, or both. The second reference indicator may be provided on the second individual package, the plunger, or both.

Advantageously, because the plunger is packaged separately from the carriage, the consumer can dispense the incontinence insert either digitally or with the plunger. As a result, in certain aspects of the present invention, the receptacle provides discreet portability and convenience.

Another aspect of the present invention includes a receptacle that contains a plurality of first individual packages and a plurality of second individual packages. Each of the first individual packages contains a carriage having an incontinence insert disposed within the carriage and includes a first reference indicator. Each of the second individual packages contains a plunger that mates with the carriage to dispense the incontinence insert and includes a second reference indicator. Desirably, the first reference indicator differs from the second reference indicator. In addition, the number of second individual packages may be less than the number of first individual packages because the plungers may be reused or because the plunger may not be required since the incontinence insert can be dispensed without the use of the plunger, such as digitally.

The present invention also contemplates a kit that includes at least one individually packaged carriage within which an incontinence insert is located, at least one individually packaged plunger, and a common receptacle that encompasses the at least one individually packaged carriage and at least one individually packaged plunger. Also contemplated within the present invention is a method of providing an incontinence insert applicator.

BRIEF DESCRIPTION OF THE DRAWINGS

FIG. 2 is an exploded view of an individual package containing a carriage within which an incontinence insert is disposed. The package and the plunger are each provided with a reference indicator.

FIG. 3 is an exploded view of an individual package containing a plunger that mates with the carriage to dispense the incontinence insert. The package and the carriage are each provided with a reference indicator.

FIG. 4 is an exploded view of a plunger and carriage after each of the plunger and carriage have been removed from their respective package and are ready to dispense the incontinence insert.

DESCRIPTION OF THE INVENTION

Figure 1:
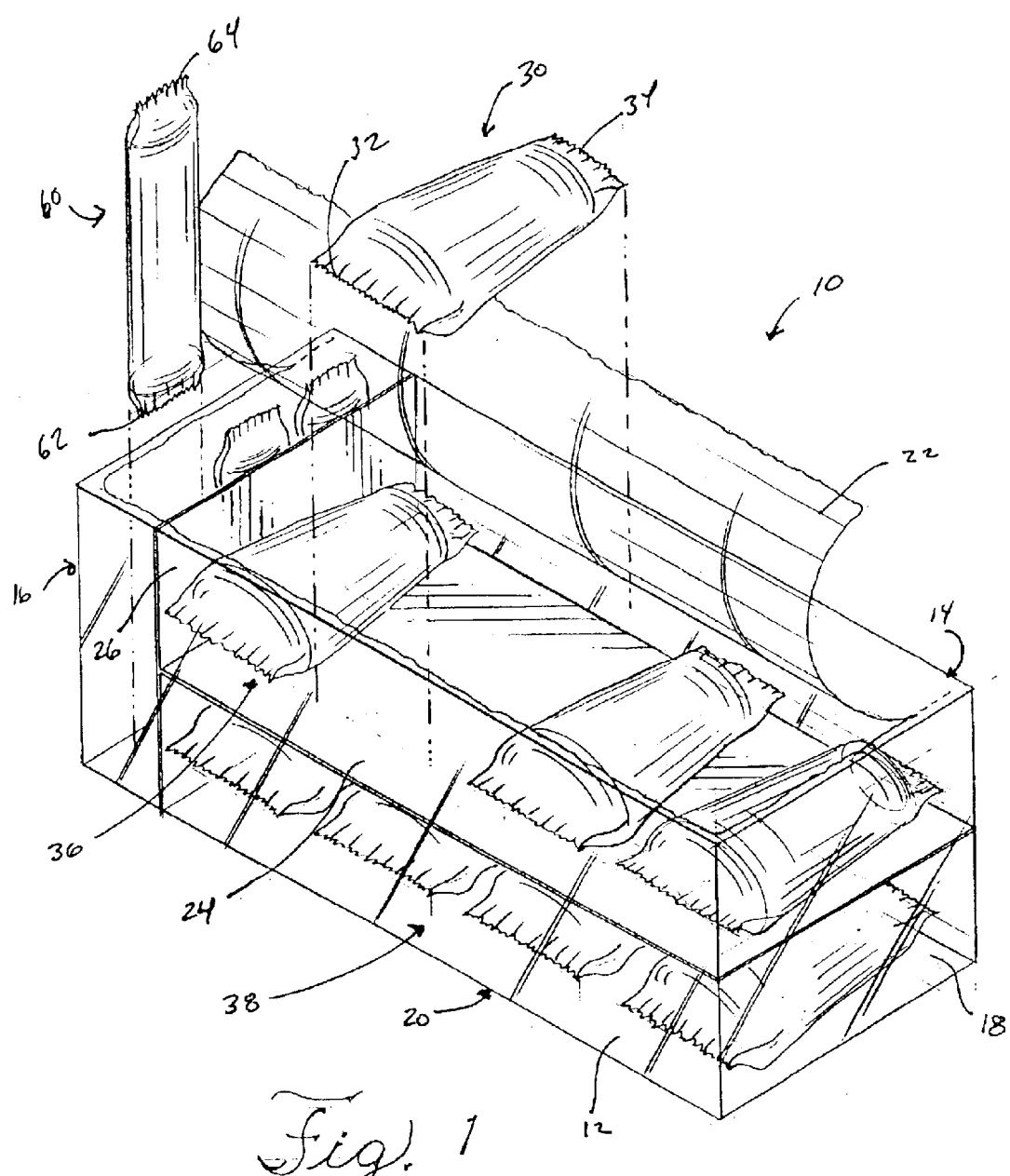
FIG. 1 is a perspective view of one embodiment of a receptacle that shows two separated layers of a plurality of first individual packages with each package containing a carriage having an incontinence insert disposed within the carriage. The receptacle also contains a plurality of second individual packages, with each package containing a plunger that mates with the carriage to dispense the incontinence insert.

Referring now to the drawings and initially to FIG. 1, a receptacle 10 according to the present invention is shown in a pre-assembled configuration. The receptacle 10 includes and stores at least one first individual package 30 that contains a carriage 40 and at least one second individual package 60 that contains a plunger 70. The carriage 40 carries an incontinence insert 50 that can be dispensed within a vaginal cavity. The plunger 70 mates with the carriage 40 to dispense the incontinence insert 50. Alternatively, the incontinence insert 50 may be digitally dispensed from the carriage 40.

The carriage 40 and the plunger 70 may be made of any suitable material such as molded plastic, paperstock, etc. The carriage 40 and the plunger 70 may also be made so that the plunger 70 mates with the carriage 40 in only a particular manner so that the consumer can easily join the plunger 70 with the carriage 40 to dispense the insert 50.

The receptacle 10 may be in the form of a flexible bag made of synthetic material such as plastic film. Other forms of packaging can be used without departing from the spirit of the invention. It is further envisioned that the receptacle 10 may be made from coated paper, woven material, non-woven material, polyethylene, polypropylene, co-polymers, extruded polymer, thermo-formed materials, and/or cardboard without departing from the scope of the present invention so long as the material can physically hold at least one first individual package 30 and at least one second individual package 60.

In the embodiment shown in FIG. 1, the receptacle 10 contains a plurality of first individual packages 30 and a plurality of second individual packages 60. The receptacle 10 shown in FIG. 1 can include any number of first individual packages 30 that are selected for the convenience of an end user. For example, the receptacle 10 may include about thirty first individual packages 30 (and in turn about thirty carriages 40 with incontinence inserts 50). It is envisioned that the receptacle 10 include a suitable number of first individual packages 30 to provide a supply of incontinence inserts 50 for one conventional week (i.e., seven days). Alternatively, it is contemplated that the receptacle 10 may be sized such that it carries only a few first individual packages 30 and a single second individual package 60 so that the receptacle 10 can be discreetly carried in a purse, handbag, or pocket.

The receptacle 10 may be made in many ways without departing from the scope of the present invention. In the embodiment illustrated in FIG. 1, the receptacle 10 comprises a substantially rectangular front 12, a back 14 opposite the front, a first side 16, a second side 18 opposite the first side, a bottom 20, and a top 22. Where the receptacle 10 is made from plastic, the top 22 can be partially removed to provide access to the inside of the receptacle 10. Where the receptacle 10 is made from cardboard or similar substance, the top 22 may be reclosable, using any construction known to those skilled in the art.

FIG. 1 also shows the receptacle 10 after it has been opened to access the first 30 and second 60 individual packages inside. Although the first individual packages 30 may be arranged in many ways without departing from the scope of the present invention, in one embodiment shown in FIG. 1, the first individual packages 30 are arranged in two layers separated by a separator 24. The separator 24 may be constructed of any suitable material. For example, the separator 24 may be constructed of plastic, cardboard, sheetstock, or any other suitably stiff material that can support and separate a first layer 36 of first individual packages 30 from a second layer 38 of first individual packages 30.

The receptacle 10 also includes at least one second individual package 60 and, in the embodiment shown in FIG. 1, the receptacle 10 includes a number of second individual packages 60, each of which includes a plunger 70. The number of second individual packages 60 is desirably less than the number of first individual packages 30 because the user may digitally dispense the incontinence insert. In addition and alternatively, the plungers 70 can be reusable and thus, one plunger 70 can be used to dispense an incontinence insert 50 from a number of carriages 40. In this regard, the second individual packages 60 can be formed in a manner to be resealable.

As shown in FIG. 1, the second individual packages 60 are separated from the first individual packages 30 by a separator 26. This separator 26 may be constructed from the same or different material as that used to separate the layers of first individual packages 30. In the embodiment shown in FIG. 1, the second individual packages 60 are provided adjacent one side 16 of the receptacle 10 so that the second individual packages 60 can be easily located and obtained from the receptacle 10.

The first and second individual packages 30, 60 may be made from any suitable material such as extruded or laminated flexible poly-based films or other non-woven materials.

The first individual package 30 has a first end 32 and a second end 34. Each end is desirably sealed to provide a sanitary enclosure for the carriage. Similarly, the second individual package 60 has a first end 62 and a second end 64. Each end is desirably sealed to provide a sanitary enclosure for the plunger. As noted above, it is desired that the plunger be reusable. In this instance, it is desirable if the second individual package 60 is made of a material that can be resealed a number of times so that the plunger 70 can be removed and reinserted into the second individual package 60 and the package can be resealed to maintain some degree of cleanliness.

The first and second packages 30, 60 may be clear or provided with a color that forms all or part of the first or second reference indicator 80, 90. Where the first 30 or second 60 individual packages are clear or transparent, the respective carriage 40 or plunger 70 may be colored, which may form all or part of the first 80 or second 90 reference indicators.

As noted above, in order to distinguish the carriages 40 from the plungers 70 and the components of the applicator 100 from other sanitary absorbent articles, a first 80 and/or a second 90 reference indicator are provided. The first 80 and second reference 90 indicators relate to the carriage 40 or the plunger 70, respectively. The first reference indicator 80 can be provided on the first individual package 30, the carriage 40, or both. Similarly, the second reference indicator 90 can be provided on the second individual package 60, the plunger 70, or both.

Each of the first 80 and second 90 reference indicators are selected from the group consisting of visual indicators, tactile indicators, or a combination of both. Visual indicators include, but are not limited to color, written notice or indicia, pictograph, icon, or a combination of the above. Tactile indicators include texturing (e.g., knurling), the use of differing materials, embossing, or a combination.

The term "color" as used in the present specification and claims relates to the phenomenon of visual perception that enables one to differentiate between otherwise identical objects and therefore the term includes the lack of color such as those commonly known as white and black. Colors may be expressed in terms of "hue", i.e., that attribute of colors that permits them to be classified as red, orange, yellow, green, blue, indigo, violet, etc. or as intermediate between any contiguous pairs of colors. Colors (hues) are also commonly perceived and referred to in terms of their relative intensities, using terms such as light, medium, dark, bright, intensity, (i.e., saturation or shades) and the like, either between colors or within a range of "shades" for otherwise the same color. Thus, one can readily perceive the difference between "light" (or "pale"), medium, and dark or ("deep") shades of red, green, blue, etc.

There are various systems of defining color and intensity. One common color system is the HSB system. In Adobe® Photoshop®, the color charts define a specific color by using three characters of HSB. For example, in the HSB system, a color H can be defined along the circumference of a cone from 0 to 360, S refers to saturation, which is the distance from 0 to 100 from the center of the cone, and B, which is the black-white scale and ranges from 0 to 100.

There are an unlimited number of colors available and varying H, S, and B can vary the various intensities of what appears to be the same color. For example, in the HSB system, if H is constant about 240 and B is constant about 100, while S is changed from about 100 to about 60, the color remains a distinct blue but changes in the depth or intensity of the color. Similarly, if H is constant about 250 and S is about 100 and B is about 100, the color is a color that is definitely blue, but as B changes from about 100 to about 80, the color changes so it is a darker more gray blue that causes a darker intensity. In another example, if S and B are about 100, a distinct range of dark to light blue occurs as the H changes from about 190 to 260. One skilled in the art will appreciate that a similar set of examples can be made for several other colors by simply going to Photoshop® and going to the "color picking" area.

The written notice or indicia may include a word or a label or a set of words or labels that communicate in writing the difference between the carriage 40 and the plunger 70. The pictograph or icon may be comprised of one or more icons of such a nature as to communicate the difference between the carriage 40 and the plunger 70.

Each of the reference indicators 80, 90 can be realized by creating markings on the packaging, on the carriage 40 or the plunger 70, or on both so that the first and second reference indicators are readily visible to the user. For example, the markings may by created by a printing process. Alternatively, the markings may be created by molding, molded plastic, embossing, die-cutting, application of a separate stick-on tab or label or any other suitable method.

The application of the markings by embossing presents the advantage of allowing the markings to be understood by the sense of touch. This is useful for blind people or in dark environments where there is not enough light to read the markings. In this regard, the first and second reference indicators 80, 90 may include the tactile indicators described above or by texturing all or a portion a portion of each of the packages, the carriage or plunger, or both, by the use of different materials for the packages 30, 60 or the carriage 40 or plunger 70 or both, or by any other suitable method.

In one embodiment, the plunger 70 may be provided with a second reference indicator 90 in the form of a color such as pink or blue. The second individual package 60 can be a transparent or clear package so that the plunger 70 can be easily identified. At the same time, the first individual package 30 can be wrapped in a non-white package such as blue, so that the carriage 40 can be easily distinguished both from the plunger 70 and from other sanitary absorbent articles such as tampons.

The present invention also includes a consumer product kit that includes at least one individually packaged carriage 40 within which an incontinence insert 50 is located, at least one individually packaged plunger 70, and a common receptacle 10 that encompasses the at least one individually packaged carriage 40 and at least one individually packaged plunger 70. The at least one individually packaged carriage 40 includes a first reference indicator 80 and the at least one individually packaged plunger 70 includes a second reference indicator 90. Accordingly, the user can distinguish between the plunger 70 and the carriage 30. Desirably, the first reference indicator 80 differs from the second reference indicator 90. In addition, when the plunger 70 is removed from its package 60 and the carriage 40 is removed from its package 30, the plunger 70 is received within the carriage 40 such that the incontinence insert 50 can be appropriately dispensed into the vaginal cavity.

As noted above, it is contemplated that the first reference indicator 80 and the second reference indicator 90 be provided on the carriage 40 and the plunger 70, respectively. When the first reference indicator 80 is provided on the carriage 40 and the second reference indicator 90 is provided on the plunger 70, each may be provided in a respective suitable location so that when the plunger 70 is correctly aligned with the carriage 40, the first 80 and second 90 reference indicators are aligned.

The present invention also contemplates a method of providing an applicator 100 for an incontinence insert 50. The method includes providing at least one individually packaged carriage 40 within which an incontinence insert 50 is located, providing at least one individually packaged plunger 70. The at least one individually packaged carriage 40 includes a first reference indicator 80 and the at least one individually packaged plunger 70 includes a second reference indicator 90. The plunger 70 is dimensioned such that it mates with the carriage 40 so that the incontinence insert 50 can be dispensed. Desirably, the first reference indicator 80 differs from the second reference indicator 90.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed:

1. A receptacle for holding at least one carriage and at least one plunger to form an incontinence insert applicator, comprising:

a. a first individual package containing a carriage and an incontinence insert means for reducing the involuntary loss of urine and including a first reference indicator; and, b. a second individual package containing a plunger and including a second reference indicator, wherein the first individual package and the second individual package are disposed in a container, and wherein the carriage and the plunger may be combined to form an incontinence insert applicator.

2. The receptacle of claim 1 further comprising an incontinence insert disposed in the carriage, wherein the insert may be dispensed from the carriage either digitally or with the plunger.

3. The receptacle of claim 1 further comprising a separator to separate the first individual package from the second individual package.

4. The receptacle of claim 1 comprising
a. a plurality of first packages arranged in a first layer and in a second layer; and,
b. a separator to separate the first layer from the second layer.

5. The receptacle of claim 1 wherein the first reference indicator is selected from the group consisting of tactile, color, written notice, pictograph, or a combination thereof.

6. The receptacle of claim 5 wherein the first reference indicator is provided on the first individual package, the carriage, or both.

7. The receptacle of claim 6 wherein the second reference indicator is selected from the group consisting of tactile, color, written notice, pictograph, or a combination thereof; wherein the second reference indicator is provided on the second individual package, the plunger, or both; and wherein the second reference indicator differs from the first reference indicator.

8. The receptacle of claim 5 wherein the second reference indicator is selected from the group consisting of tactile, color, written notice, pictograph, or a combination thereof and wherein the second reference indicator differs from the first reference indicator.

9. The receptacle of claim 1 wherein the second reference indicator is selected from the group consisting of tactile, color, written notice, pictograph, or a combination thereof.

10. The receptacle of claim 9 wherein the second reference indicator is provided on the second individual package, the plunger, or both.

11. The receptacle of claim 1 wherein the first individual package is opaque or colored and the second individual package is transparent.

12. A receptacle for separately holding at least one carriage and at least one plunger to form an incontinence insert applicator, comprising:

a. a first individual package containing a carriage and an incontinence insert means for reducing the involuntary loss of urine and including a first reference indicator, wherein the first reference indicator is selected from the group consisting of tactile, color, written notice, pictograph, or a combination thereof and wherein the first reference indicator is provided on the first individual package, the carriage, or both; and, b. a second individual package containing a plunger and including a second reference indicator, wherein the second reference indicator is selected from the group consisting of tactile, color, written notice, pictograph, or a combination thereof; wherein the second reference indicator is provided on the second individual package, the plunger, or both; and wherein the second reference indicator differs from the first reference indicator, wherein the first individual package and the second individual package are disposed in a container, and wherein the carriage and the plunger may be combined to form an incontinence insert applicator.

13. The receptacle of claim 12 wherein the first individual package is opaque or colored and the second individual package is transparent.

14. The receptacle of claim 12 further comprising an incontinence insert disposed in the carriage, wherein the insert may be dispensed from the carriage either digitally or with the plunger.

15. A receptacle comprising:

a. a plurality of first individual packages arranged in a first layer and in a second layer, each of the first individual packages containing a carriage having an incontinence insert means for reducing the involuntary loss of urine disposed within the carriage and including a first reference indicator;

b. a separator to separate the first layer from the second layer;

c. a plurality of second individual packages, each of the second individual packages containing a plunger and including a second reference indicator; and, c. a separator to separate the plurality of second individual packages from the first individual packages, wherein the plurality of first individual packages and the plurality of second individual packages are disposed in a container, and wherein the carriage and the plunger may be combined to form an incontinence insert applicator.

16. The receptacle of claim 15 wherein the number of the plurality of second individual packages is less than the number of the plurality of first individual packages.

17. The receptacle of claim 15 wherein the first reference indicator differs from the second reference indicator.

18. The receptacle of claim 15 further comprising an incontinence insert disposed in the carriage, wherein the insert may be dispensed from the carriage either digitally or with the plunger.

* * * * *